United States Patent [19]

Khanna

[11] Patent Number: 4,816,391

[45] Date of Patent: Mar. 28, 1989

[54] AMINE STABILIZED AMINOGLYCOSIDE FORMULATIONS

[75] Inventor: Pyare Khanna, San Jose, Calif.

[73] Assignee: Syntex (U.S.A.) Inc., Palo Alto, Calif.

[21] Appl. No.: 9,617

[22] Filed: Jan. 22, 1987

Related U.S. Application Data

[63] Continuation of Ser. No. 583,907, Feb. 29, 1984, abandoned.

[51] Int. Cl.$^4$ ............... G01N 33/53; C07H 15/20; C07G 11/00
[52] U.S. Cl. .................................... 435/7; 436/546; 436/826; 536/13.6; 536/13.7; 536/16.8
[58] Field of Search .................... 435/7, 188, 810, 4; 436/536, 546, 815, 825, 826

[56] References Cited

U.S. PATENT DOCUMENTS 4,100,268  7/1978  Scherr ........................ 436/815 X
4,218,335  8/1980  Mochida et al. .................. 435/7

OTHER PUBLICATIONS

Hyde et al., *Endocrinology* (111:4), 1421–1423, 1982.
Naor et al., *Molecular and Cellular Endocrinology* (25), 85–97, 1982.
Chang et al., *Biochemical and Biophysical Research Communications*, (134:1), 134–139, 1986.

*Primary Examiner*—Robert J. Warden
*Assistant Examiner*—Janelle Graeter
*Attorney, Agent, or Firm*—Theodore J. Leitereg

[57] ABSTRACT

Novel formulations are provided containing conjugated or unconjugated aminoglycosides, particularly labeled glycosides, a small amount of a polyamine, and additional additives, such as buffer, salt, and inert protein. The level of immunologic activity of the aminoglycoside is retained for long periods of time when stored in glass containers.

17 Claims, No Drawings

AMINE STABILIZED AMINOGLYCOSIDE FORMULATIONS

This is a continuation of pending application Ser. No. 583,907, filed Feb. 29, 1984, incorporated herein by reference and now abandoned.

BACKGROUND OF THE INVENTION

1. Field of the Invention

Aminoglycosides are an important analyte for determining the appropriate level of administration. Since the aminoglycosides have significant side effects, it is desirable to monitor the blood level of the aminoglycosides to ensure that the level is within the therapeutic level. To assay for aminoglycosides, in many assays the aminoglycoside is labeled with, for example, an enzyme or fluorophore. In many of these assays, calibrators are supplied which are used to prepare a standard curve. That is, the series of calibrators have different concentrations of the analyte and assays are performed using the calibrators and a curve is derived reflecting the change in signal with the varying analyte concentration. Commonly, the calibrators are provided as powders to the laboratory, where the technician dissolves the powder into a specified amount of solvent to obtain a calibrator solution. The solution will be used repetitively and may stand for long periods of time in glass containers. It is therefore important that the calibrators continue to reflect the same signal level which will be observed in the assay with the sample. The observed signal level of the calibrator must not vary with the time of standing of the reconstituted calibrator solution or the results reported for the concentration of analyte will be in error. It is therefore important that the aminoglycoside and aminoglycoside reagents be capable of providing constant results for long periods of time during storage.

2. Description of the Prior Art

U.S. Pat. Nos. 4,220,722 and 4,328,311 describe enzyme conjugates of aminoglycosides and their use in immunoassays.

SUMMARY OF THE INVENTION

Calibrated formulations comprising aminoglycosides or labeled aminoglycosides, particularly labeled with an enzyme, and other additives, are stabilized after reconstitution by inclusion of a polyamine in a lyophilized powder composition or in the reconstituted calibrator solution. Particularly, low molecular weight polyamines are employed in minor amount.

DESCRIPTION OF THE SPECIFIC EMBODIMENTS

Novel formulations are provided involving combinations of aminoglycosides or derivatives thereof, polyamines, and usually including various additives, such as buffer, salt, proteins, stabilizers, or the like. The presence of the polyamines prevents the loss of active aminoglycoside, believed to be due to adsorption of the aminoglycoside to glass container walls. That is the titer as determined by binding to antibodies remains substantially constant over long periods of time.

The aminoglycosides may be the naturally occurring aminoglycosides or modified amonoglycosides, particularly where one or more aminoglycosides are conjugated to a protein, e.g., an enzyme, or other label. The formulations are employed in immunoassays for the detection of the presence of an aminoglycoside, where the aminoglycoside is present as a reagent to be involved with a sample or as a calibrator for establishing a standard. The formulations will vary depending upon whether the aminoglycoside is present conjugated to a label or unconjugated.

Illustrative aminoglycosides include tobramycin, gentamicin, kanamycin, amikacin, etc.

The polyamines which are employed will be non-aromatic polyamines, usually saturated aliphatic or heterocyclic polyamines, which will have at least two amino groups, normally primary amino groups, and may have twelve or more amino groups, unless a polymeric polyamine is employed, where the number of amino groups may be 40 or more. Of particular interest are non-aromatic hydrocarbylene polyamines. ("Hydrocarbylene" intends an organic group containing only carbon and hydrogen and having two available sites for joining to a functionality.) Other polyamines include amino-substituted dextran, polyethylene amine, polybrene polyethylene polyamine, etc.

The polyamines which are employed will be water soluble and generally range from about 2 to 20 carbon atoms, more usuallly from about 2 to 12 carbon atoms and have from about 2 to 6 amino groups, more usually from about 2 to 4 amino groups. The polyamines may be aliphatic, alicyclic or heterocyclic, where the heteroatoms will be nitrogen. While other heteroatoms may be present, e.g., oxygen, for the most part the lower molecular weight polyamines will be free of other inert heteroatoms. Usually, the ratio of amino groups to carbon atoms will be from about 1:1-6, more usually from about 1:1-3.

In the formulations, one or more polyamines may be employed. The ratio of amino groups of the polyamines to the molecules of aminoglycosides will generally be in the range of about 10:1 and usually not more than 1000:1, generally being in the range of about 20-500:1, more usually in the range of about 50-500:1.

The formulations are conveniently provided as powder formulations to be reconstituted before use and to provide for stable responses upon long storage in glass. For use in immunoassays, the formulations will usually provide for a number of additional materials, depending upon whether the formulation is to be used as a calibrator or is to serve as an active reagent, where the aminoglycoside is conjugated to a label. The additional materials need not be included with the aminoglycoside, either conjugated or unconjugated, but will normally be present to provide for a variety of desired characteristics upon reconstitution.

Where the aminoglycoside is to be used as a calibrator, its concentration in the formulation will vary in accordance with the desired concentration of the aminoglycoside in the calibrator solution upon reconstitution. The amount of aminoglycoside will represent a value of interest related to the therapeutic dosage range of the particular aminoglycoside. Therefore, the particular amount of the aminoglycoside in the formulation is not critical, so long as the aminoglycoside formulation can be readily reconstituted in an accurate and reproducible manner. Generally, the aminoglycoside will be present in 0.001 to 0.01 wt% of the powder formulation, more usually 0.002 to 0.01 wt%. This will provide a concentration upon reconstitution of about 2 to 20 $\mu$M.

Where the aminoglycoside is present as a conjugate reagent, the weight percent of the reagent will vary widely, depending upon the nature of the label, the protocol of the assay, the nature of the assay, the intended dilution, as well as other relevant factors. Usually, the weight percent of the reagent will vary from about 0.01 to 1 wt% of the formulation, more usually from 0.01 to 0.1 wt. %. For enzyme lables, the wt% will generally be from 0.01 to 1, more usually from 0.1 to 0.5 weight percent to provide a concentration in the range of about 10 to 100 nM, while with fluorescent labels, the concentration will generally range from about 1 nM to 10 μM, more usually from 1 to 10 μM.

Illustrative of calibrators will be compositions having between 99% and 99.9% of serum protein, which can be conveniently Freon treated and lyophilized. Included with the serum will be a stabilizer, e.g., thimerosal. In minor amount will be a sufficient amount of the aminoglycoside to provide for the desired concentration of the aminoglycoside upon reconstitution.

For the active reagent, where the reagent is an enzyme label, the active materials will generally have from about 50–90 wt% of the enzyme reagent, about 5 to 25% of an inert protein carrier, e.g., serum albumin, from about 5 to 25% of salt and minor amounts of stabilizers, generally ranging from about 0.01 to 2 wt%, such stabilizers being illustrated by thimerosal and sodium azide.

For a fluorescent reagent, the fluorescent reagent may be employed neat or may be combined with the above ingredient in the amounts indicated, or any one or more of the ingredients where the relative percentages would be modified accordingly.

The above formulations may be combined with various inert excipients in weight ratios of 1:1–19 to provide for easy transfer.

Upon reconstitution, the buffer should provide a concentration of about 0.01 to 0.1 mM of the polyamine. The pH should generally be in the range of about 7–9, more usually about 7.5–8.5. The inert protein concentration will generally be from about 0.1 to 2 wt%. The aminoglycoside concentration as conjugate will generally be in the range of about 0.1–50 nM.

Reconstitution will normally be achieved with water, usually distilled water, which may be subject to additional purification.

The reagents find use in a wide variety of immunoassays which are described in U.S. Pat. Nos. 3,817,837; 3,850,752; 4,174,384; 4,220,450; and the like.

The following examples are offered by way of illustration and not by way of limitation.

EXPERIMENTAL

EXAMPLE 1

Preparation of tobramycin-glucose-6-phosphate dehydrogenase (G6PDH) conjugate

Lyophilized G6PDH is reconstituted in a minimum volume of tris-HCl buffer (0.055M, pH 8.0) and the suspension is passed through a Sephadex G-50 column. The resulting enzyme solution is adjusted to a protein concentration of 3.8 mg/ml. NADH (20 mg/mg enzyme) and glucose-6-phosphate monosodium salt (10 mg/mg enzyme) are dissolved in the enzyme, solution, and the pH is adjusted to 8.5–8.9. A solution of bromoacetyl-glycine-(N-hydroxy succinimide)ester (0.05 mg/μl N,N-dimethyl formamide (DMF)) in DMF cooled to 4° C. is added at a slow rate to the enzyme solution at 4° C. (0.10 mg ester/min for 45 mg of enzyme). The extent of labelling is monitored by the % deactivation of the enzyme. The addition is terminated when the % deactivation is between 75–80%. The molar ratio of the ester to the enzyme is in the range of 140–180:1. The labeled enzyme is dialyzed against the tris-HCl buffer.

Tobramycin sulfate is dissolved at room temperature in distilled water (150 μl/ml); the pH is adjusted to 10.2 and oxygen purged with bubbling argon for 0.5 hours. N-acetyl DL-homocysteine (HCTL; 250 μmoles/ml) in oxygen-free distilled water at 4° C. is added at a slow rate (<50 μmoles HCTL/min for 1 mmole tobramycin) to the tobramycin at room temperature. A 2.3 molar excess of tobramycin to HCTL is employed. After completion of the addition, the pH of the reaction mixture is adjusted to 10.2, and the solution stirred vigorously for 1.5 hours at room temperature with continuous bubbling of argon gas. The pH is then adjusted to 7.0 and the solution cooled in an ice bath.

The enzyme conjugate solution (pH 8.5) is purged with argon and the argon stream continued through the solution during the reaction. The tobramycin derivative prepared above is added at a slow rate (2 μmoles of tobramycin derivative/min for 0.43 μmoles of labeled enzyme) with stirring. The addition is terminated when 500 to 600 molar excess of the tobramycin derivative has been added. The solution is maintained for 3–4 days under an argon atmosphere at 4° C. The conjugate is then dialyzed against the tris-HCl buffer and stored.

The following tests were carried out to demonstrate the effectiveness of polyamines in stabilizing the enzymatic activity of the tobramycin-enzyme conjugate prepared above when reconstituted and stored in a glass container. Formulations were prepared as follows. One volume of the protein conjugate was diluted with 57.5 parts by volume of a solution of trizma base (6.6 g/l; rabbit serum albumin 10 g/l; NaCl 9 g/l; thimerosal 0.05 g/l; NaN$_3$ 0.5 g/l, pH adjusted to 8) to provide 434 μl of solution, which was diluted with water to 25 ml. A 5-ml aliquot was added to each of two 10 ml volumetric flasks and the volume brought to 10 ml with the diluent described above. Into the second flask was introduced 10 μl of tris-(2-aminoethyl)aminoethylamine 0.1%). Anti(tobramycin) was prepared by diluting a sufficient amount of the anti(tobramycin) with a diluent (0.055M tris-HCl; 0.05% sodium azide; 0.05% thimerosal; 1.0% RSA; 0.04M NAD; 0.066M glucose-6-phosphate; pH 5.0) so that approximately 70% of the G6PDH conjugate activity is inhibited in the absence of tobramycin. Calibrators were also reconstituted having varying concentrations of tobramycin. The maximum rate was measured fo each bottle, and then a standard curve was determined using the calibrators after one hour of reconstitution and after 8 hours of reconstitution. The assay method is described in U.S. Pat. No. 3,817,837, which disclosure is incorporated herein by reference. The following table indicates the results.

TABLE I

| Sample* | ΔA$^+$ | | | |
| | No Amine | | Amine | |
| | 1 hr. | 8 hr. | 1 hr. | 8 hr. |
| --- | --- | --- | --- | --- |
| Rmax | 772 | | 790 | 793 |
| neg. | 422 | 411 | 504 | 500 |
| 1 | 450 | 441 | 527 | 526 |
| 2 | 482 | 469 | 553 | 551 |
| 4 | 551 | 539 | 615 | 621 |
| 8 | 677 | 659 | 714 | 715 |
| 16 | 720 | 710 | 751 | 751 |

TABLE I-continued

| Sample* | ΔA+ | | | |
|---|---|---|---|---|
| | No Amine | | Amine | |
| | 1 hr. | 8 hr. | 1 hr. | 8 hr. |
| control | 628 | 610 | 677 | 681 |

*Rmax intends the max rate for the conjugated enzyme. The neg. and numbers indicate the calibrators having no tobramycin or tobramycin in an amount providing a sample concentration of the indicated number in μg/ml.
+Indicates the change in absorption in mOD between two readings taken one hour after mixing and 8 hours after mixing. Average of two values.

Substantially the same procedure was repeated, except that in this study, ethylene diamine was employed. The concentration of ethylene diamine was 9 ml of ethylene diamine to 91 ml of the enzyme conjugate diluted 1:100.

TABLE II

| Ethylene Diamine (%) | tube | ΔA | | |
|---|---|---|---|---|
| | | 1 day | 4 days | 8 days |
| 0.001 | 1 | 793 | 779 | 774 |
| | 2 | 803 | 773 | 777 |
| 0.005 | 1 | 808 | 776 | 785 |
| | 2 | 811 | 771 | 776 |
| 0.01 | 1 | 805 | 773 | 791 |
| | 2 | 810 | 786 | 794 |
| 0.05 | 1 | 825 | 811 | 808 |
| | 2 | 806 | 786 | 786 |
| 0.08 | 1 | 808 | 799 | 796 |
| | 2 | 804 | 791 | 790 |
| 0.09 | 1 | 813 | 809 | 817 |
| | 2 | 794 | 794 | 796 |
| 0.10 | 1 | 819 | 817 | 817 |
| | 2 | 799 | 792 | 795 |
| 0.12 | 1 | 809 | 812 | 818 |
| | 2 | 808 | 804 | 806 |

The above results demonstrate the significance of having a small amount of a polyamine present in the reconstituted reagents. In the absence of amine and in the presence of a large amount of tobramycin, one should be approaching the maximum rate. The fact is, however, that the observed rate is still substantially lower than the maximum rate. In the presence of a small amount of the amine, the rate is substantially enhanced and remains constant over an 8 hour period. By contrast, in the absence of amine, the rate is dropping, so that one is required to repeatedly prepare a new standard curve over relatively short periods of time.

A number of things are evident from the above results. First, in the absence of the polyamine, enzymatic activity drops off substantially and is not recovered at concentrations of tobramycin which should provide for substantial recovery of enzymatic activity approaching the maximum rate. Secondly, with time, there is a further drift downward, indicating that one could not use reconstituted solutions from calibrators which had stood for extended periods of time and expect accurate results. Therefore, one whould be required to repeatedly prepare fresh solutions each time one wished to establish a calibration curve.

By contrast, the diminution of the enzymatic activity in the presence of polyamine is relatively insignificant and the activity is retained for long periods of time. Thus, great efficiencies are achieved since, once the calibrated solutions and enzyme reagent solutions are reconstituted, one can repeatedly use the solutions and obtain results which will be relevant to the actual concentration of tobramycin.

The invention has been described in detail with particular reference to the above embodiments. It will be understood, however, that variations and modifications can be effected within the spirit and scope of the invention.

What is claimed is:

1. A composition for use in an immunoassay which comprises an aminoglycoside and a polyamine in an amount sufficient to inhibit the loss of aminoglycoside available for binding to antibodies for aminoglycosides, said polyamine being an unconjugated, non-aromatic, non-proteinaceous, saturated aliphatic or heterocyclic polyamine having at least two amino groups.

2. A composition according to claim 1, wherein said aminoglycoside is tobramycin.

3. A composition according to claim 1, wherein said polyamine has from 2 to 12 carbon atoms.

4. A composition according to claim 1, wherein said aminoglycoside is conjugated to an enzyme.

5. A composition according to claim 1, wherein said aminoglycoside is conjugated to a fluorescent label.

6. A composition according to claim 1, wherein said polyamine is ethylene diamine or polyethylene polyamine.

7. A composition according to claim 1, wherein said polyamine is a hydrocarbylene polyamine.

8. A composition according to claim 1, wherein said polyamine has from 2 to 6 amino groups.

9. A composition for use in an immunoassay, which comprises an aminoglycoside and a polyamine in an amount sufficient to inhibit the loss of aminoglycoside available for binding to antibodies to aminoglycosides, said polyamine being ethylene diamine or a polyethylene polyamine.

10. A composition for use in an immunoassay, which comprises an aminoglycoside and a polyamine in an amount sufficient to inhibit the loss of aminoglycoside available for binding to antibodies to aminoglycoside, said polyamine being a hydrocarbylene polyamine.

11. A method of stabilizing an aminoglycoside, which comprises combining said aminoglycoside with a polyamine in an amount sufficient to inhibit the loss of aminoglycoside available for binding to antibodies to aminoglycosides, said polyamine being an unconjugated, non-proteinaceous saturated aliphatic or heterocyclic polyamine having at least two amino groups.

12. A method according to claim 11, wherein said aminoglycoside is tobramycin.

13. A method according to claim 11, wherein said polyamine has from 2 to 12 carbon atoms.

14. A method according to claim 11, wherein said aminoglycoside is conjugated to an enzyme.

15. A method according to claim 11, wherein said polyamine is ethylene diamine or polyethylene polyamine.

16. A method according to claim 11, wherein said polyamine is a hydrocarbylene polyamine.

17. A method according to claim 11, wherein said polyamine has from 2 to 6 amino groups.

* * * * *